US 6,673,620 B1

(12) United States Patent
Loeffler et al.

(10) Patent No.: US 6,673,620 B1
(45) Date of Patent: Jan. 6, 2004

(54) FLUID EXCHANGE IN A CHAMBER ON A MICROSCOPE SLIDE

(75) Inventors: Herbert H. Loeffler, Arlington, MA (US); Steven A. Bogen, Sharon, MA (US)

(73) Assignee: CytoLogix Corporation, Cambridge, MA (US)

( * ) Notice: Subject to any disclaimer, the term of this patent is extended or adjusted under 35 U.S.C. 154(b) by 0 days.

(21) Appl. No.: 09/549,414

(22) Filed: Apr. 14, 2000

Related U.S. Application Data
(60) Provisional application No. 60/130,171, filed on Apr. 20, 1999.

(51) Int. Cl.[7] .............................................. G01N 35/00
(52) U.S. Cl. .................... 436/46; 436/174; 436/180; 422/99; 422/100; 422/102; 422/104; 359/398
(58) Field of Search ................... 359/396, 398; 436/46, 180, 174; 427/2.11; 422/100, 104, 102, 99

(56) References Cited

U.S. PATENT DOCUMENTS

| | | | | |
|---|---|---|---|---|
| 3,227,130 A | * | 1/1966 | Weiskopf | 118/429 |
| 3,526,203 A | * | 9/1970 | Kinney et al. | 118/429 |
| 3,892,197 A | * | 7/1975 | Kinney et al. | 118/429 |
| 4,384,193 A | | 5/1983 | Kledzik et al. | 219/521 |
| 4,483,270 A | * | 11/1984 | Toya et al. | 118/694 |
| 4,604,964 A | | 8/1986 | Gordon et al. | 118/50 |
| 4,731,335 A | | 3/1988 | Brigati | 436/180 |
| 4,847,208 A | | 7/1989 | Bogen | 436/174 |
| 4,974,952 A | * | 12/1990 | Focht | 350/536 |
| 4,985,206 A | | 1/1991 | Bowman et al. | 422/99 |
| 5,023,187 A | | 6/1991 | Koebler et al. | 436/180 |
| 5,049,510 A | * | 9/1991 | Repasi et al. | 118/429 |
| 5,068,091 A | | 11/1991 | Toya | 422/99 |
| 5,073,504 A | * | 12/1991 | Bogen | 436/174 |

(List continued on next page.)

FOREIGN PATENT DOCUMENTS

| | | | |
|---|---|---|---|
| WO | WO 94/18539 | * | 8/1994 |
| WO | WO 96/30124 | | 10/1996 |
| WO | WO 98/20353 | | 5/1998 |
| WO | WO 99/34190 | * | 7/1999 |

OTHER PUBLICATIONS

Abbuhl, Mary Faith et al., "An Economical Minichamber for Immunohistochemical Incubation," The Journal of Histochemistry and Cytochemistry, vol. 33, No. 2, 1985, pp. 162–164.

Ormanns, W. et al., "A Simple Method for Incubation of Tissue Sections in Immunohistochemistry," Histochemistry, 72, 1981, pp. 315–319.

Montone, Kathleen T., M.D., et al., "Anatomic Viral Detection Is Automated: The Application of a Robotic Molecular Pathology System for the Detection of DNA Viruses in Anatomic Pathology Substrates, Using Immunocytochemical and Nucleic Acid Hybridization Techniques," The Yale Journal of Biology and Medicine 62, 1989, pp. 141–158.

Unger, Elizabeth R., et al., "Automation of In situ Hybridization: Application of the Capillary Action Robotic Workstation," Journal of Histotechnology, vol. 11, No. 4, Dec. 1988, pp. 253–258.

Brigati, David J., M.D., "In Situ DNA Hybridization is Automated," *Automated Molecular Pathology*, (Sep. 1988).

*Primary Examiner*—Jill Warden
*Assistant Examiner*—Elizabeth Quan
(74) *Attorney, Agent, or Firm*—Hamilton, Brook, Smith & Reynolds, P.C.

(57) ABSTRACT

A sample chamber is formed by a housing sealed against a microscope slide. The housing has fluid ports, including a well formed over at least one port. In a rinse station, rinse solution is drawn from a reservoir through the chamber to a waste reservoir. At a fill station, an aliquot of reagent already placed in the well is driven into the chamber. The reagent may be driven into the chamber by first drawing a vacuum on the chamber through the aliquot of reagent and then releasing the reagent to be drawn into the chamber by the vacuum.

23 Claims, 10 Drawing Sheets

U.S. PATENT DOCUMENTS

| | | | | |
|---|---|---|---|---|
| 5,273,718 A | * | 12/1993 | Skold et al. | 422/100 |
| 5,273,905 A | | 12/1993 | Muller et al. | |
| 5,316,452 A | | 5/1994 | Bogen et al. | 417/412 |
| 5,338,358 A | | 8/1994 | Mizusawa et al. | 118/401 |
| 5,346,672 A | * | 9/1994 | Stapleton et al. | 422/102 |
| 5,354,370 A | * | 10/1994 | Schmehl | 118/421 |
| 5,559,032 A | * | 9/1996 | Pomeroy et al. | 422/100 |
| 5,560,956 A | * | 10/1996 | Schmehl | 427/2.11 |
| 5,597,536 A | * | 1/1997 | Mayer | 422/102 |
| 5,603,351 A | * | 2/1997 | Cherukuri et al. | 137/597 |
| 5,645,114 A | | 7/1997 | Bogen et al. | 141/145 |
| 5,660,796 A | * | 8/1997 | Sheehy | 422/100 |
| 5,788,927 A | * | 8/1998 | Farrell et al. | 422/100 |
| 5,830,413 A | | 11/1998 | Lang et al. | 422/100 |
| 5,947,167 A | | 9/1999 | Bogen et al. | 141/1 |
| 5,958,341 A | * | 9/1999 | Chu | 422/99 |
| 5,958,760 A | | 9/1999 | Freeman | 435/286 |
| 5,985,669 A | | 11/1999 | Palander | 436/46 |
| 6,054,325 A | * | 4/2000 | Kedar et al. | 422/100 |
| 6,083,761 A | * | 7/2000 | Kedar et al. | 422/100 |
| 6,096,271 A | * | 8/2000 | Bogen et al. | 422/100 |
| 6,376,256 B1 | * | 4/2002 | Dunnington et al. | 209/45 |
| 6,395,536 B2 | | 5/2002 | Freeman | |
| 6,432,696 B2 | | 8/2002 | Custance et al. | |

* cited by examiner

SECTION A-A

FLUID EXCHANGE IN A CHAMBER ON A MICROSCOPE SLIDE

RELATED APPLICATION(S)

This application claims the benefit of U.S. Provisional Application No. 60/130,171, filed Apr. 20, 1999, the entire teachings of which are incorporated herein by reference.

GOVERNMENT SUPPORT

The invention was supported, in whole or in part, by NIH grant 1R43CA84686-01 from Public Health Service. The Government has certain rights in the invention.

BACKGROUND OF THE INVENTION

This invention relates to an instrument that is capable of performing incubations of small volumes of reagents on the surface of a microscope slide. A variety of assays are typically carried out on the surface of a microscope slide. These assays generally aim to determine if a suspected analyte is present in a patient biopsy. They include: (1) in situ hybridization, for the detection of nucleic acid targets in a tissue or cell sample, (2) immunohistochemistry, for the detection of specific proteins in a tissue or cell sample, (3) histochemical stains, for the detection of certain types of chemical compounds or classes of microorganisms in a tissue sample. In addition, there are two other types of assays that are often carried out on the surface of a glass slide. Rather than testing for the presence of an analyte in a tissue biopsy, these assays aim to detect specific molecules in a solution. They are (1) gene arrays, whereby an array of known nucleic acid targets are immobilized directly on the glass slide, and (2) protein arrays, hereby an array of known proteins are immobilized on the glass slide.

In each of these instances, a glass slide serves as the preferred support on which the assay is carried out. The reason a glass slide is used is that it is optically clear and flat. These physical properties facilitate the ability of an instrument, such as a microscope, to optically detect a fluorescent or colorimetric signal. In order to highlight certain desired features, the above assays require that the slides be treated with a series of reagent incubations. Each incubation needs to occur for a specific time (typically 15–60 minutes) and at a specified temperature (typically, from room temperature to 95° C.).

The optical advantages of a microscope slide are somewhat counterbalanced by certain difficulties in performing the assay. The treatment of the tissue sections on a microscope slide for the purpose of highlighting certain histologic features is often called "staining." Since the surface of the slide is flat, reagent can easily drain off the edge of the microscope slide, especially if the slide is not perfectly level. Moreover, the large surface area to volume ratio of reagent spread over the slide surface promotes evaporation. Evaporation of reagent interferes with the performance of the assay. If the reagent evaporates, then it will not continuously contact the tissue sample. Drying artifacts may cause the assay result ("stain") to not be accurate. Lastly, it is important to spread the reagent over the slide surface. Surfactants are sometimes used to promote reagent spreading. If the reagent does not spread, then the reaction may fail to occur over all of the tissue biopsy, or over all portions of the array. Therefore, the prior art comprises a great number of attempts to construct apparatus and devices that aim to facilitate or automate the sample preparation/treatment steps of a biological sample on a glass slide.

The general approach to solving these problems in the past has been to enclose an area of the slide surface, forming a chamber. Desirable features for such a chamber are:

a) Liquid spreading. Reagents must be evenly spread, without entrapped air bubbles.

b) Use of minimal reagent volume (ideally less than 100 microliters to cover the slide surface).

c) Prevent evaporation when the reagent is heated to 95° C.

d) Automatic reagent injection and removal. Namely, the apparatus needs to be compatible with an automated fluid transfer system.

e) Protection of the tissue section against physical damage.

One method of addressing at least some of the requirements described above is to entrap reagent under a coverslip. For in situ hybridization procedures, reagent is conventionally placed directly on top of the tissue section with a pipette and covered with a coverslip. The edges of the coverslip are then sealed with nail polish or rubber glue. The coverslip both spreads out the reagent into a relatively uniform layer and prevents evaporation. It is important to avoid entrapping air bubbles under the coverslip. Otherwise, there will be an area of the tissue section that does not contact the hybridization solution.

No existing technology is suited to automating coverslipping for in situ hybridization. Coverslips can be applied to slides in an automated fashion; several companies serving the histopathology market sell dedicated coverslipping machines. However, such coverslipping machines are not likely to be adaptable to this application, because (i) it will be difficult to automate sealing the coverslip edges, such as with glue, and (ii) it will be difficult to robotically remove the coverslips without damaging the tissue section.

An alternative method for spreading small amounts of reagents was described in 1988, by Unger, et.al. (Unger, E. R., D. J. Brigati, M. L. Chenggis, et.al. 1988. Automation of in situ hybridization: Application of the capillary action robotic workstation. *J. Histotechnology* 11:253–258.) Specifically, they described a modification of the Code-On slide stainer for use with in situ hybridization. Instead of a coverslip, two slides were placed in close apposition to each other, forming a capillary gap. Liquids, such as a hybridization solution, could then be applied to the bottom of the gap. The reagents "wicked" in by capillary action. Placing the slides in a heated humidity chamber prevented evaporation. The Code-On worked well in the right hands, but was labor-intensive and required a great deal of experience and care each day in setting it up. Slight scratches or imperfections in the surface of the glass slide sometimes caused air bubbles to be entrapped in the capillary gap, resulting in areas of the tissue not being stained.

An early description of a slide chamber is disclosed in U.S. Pat. Nos. 4,847,208 and 5,073,504. A chamber was apposed to the surface of a slide, forming walls capable of preventing lateral spillover of reagent. Moreover, a hinged cover minimized the evaporative loss of reagent. Each chamber included a fluid inlet and outlet port.

WO99/34190 discloses a chamber formed by the insertion of a microscope slide into a cartridge device. Reagent is dispensed onto a portion of the slide that protrudes from the cartridge and is caused to flow into a capillary gap-type space by moving the slide inwards. The chamber is not sealed from the outside environment. Therefore, reagent will be expected to evaporate, especially if the samples are heated. Moreover, reagent can flow around and underneath the slide, thereby increasing the volume requirement to cover the slide surface. Lastly, it is unclear how often bubbles will be entrapped over the slide surface, since no specific mechanism in the cartridge prevents them.

A review of other methods of forming a chamber, and their drawbacks, are also described in the Background section of WO99/34190.

SUMMARY OF THE INVENTION

In embodiments of the present invention, a fluid handling apparatus is capable of spreading small amounts of liquid reagent over a flat surface, such as a microscope glass slide. The reagent may be sealed within a confined cavity, or "chamber", so as to prevent evaporation even with heating of small amounts of reagent during an incubation period. One surface of this chamber is the flat slide surface. The remaining surfaces are formed by a cell. The cell is preferably a plastic disposable part that fits on top of the slide, over the area containing the tissue, biologic cells, or array mounted on the glass slide. The cell forms a fluid seal to the surface of the glass by means of a gasket. The gasket is mounted in a recess on the face of the cell that mates with the glass slide.

Each cell has two fluid ports. These ports are in fluid communication with the chamber. Therefore, when liquid reagent is inserted into a fluid port, it can travel into the chamber and contact the biologic sample or array mounted on the glass surface. The fluid ports on a cell are preferably positioned on opposite ends of the cell. This allows for liquid reagent or wash solution to flow in one fluid port, fill the chamber, and then exit the other fluid port at the other end of the cell. Each fluid port has a valve occluding the orifice that is normally closed. Consequently, the chamber is sealed. Unless the valves are opened, the chamber is normally not accessible to the outside environment. Liquid reagents or wash solutions are only added or removed by opening one or both of the valves associated with the fluid ports. The fact that the fluid ports are normally sealed by valves helps prevent evaporation.

The instrument comprises a plurality of positions for glass slides. Each position has a mechanism to clamp a cell to the glass slide. Keeping the cell and slide apposed to each other in a fixed spatial relationship is important in forming a sealed chamber for reagent incubations. Reagents and wash solutions are added and removed by the use of two liquid handling "stations". In the illustrated embodiment, the liquid handling stations move over non-moving slides. It is also conceivable, and ultimately preferred in an automated instrument, to reverse that relationship to automate the staining process by moving the slides, such as on a rotary carousel. The slides would move past non-moving liquid handling stations positioned on the periphery of the rotary carousel of slides. This type of arrangement is described in U.S. Pat. No. 5,947,167 by the same inventors which is incorporated by reference in its entirety.

The method of adding and subsequently washing reagents out from the chamber is an important part of this system. Washing reagent out from the chamber is required after an incubation, to thoroughly remove any unreacted reagent before the subsequent treatment step. Washing usually involves treating the biologic sample mounted on the glass slide with an excess of a buffer or wash solution. The unreacted reagent is diluted in the excess volume of the wash solution and removed by aspirating away the wash solution. In this system, washing the biologic sample involves flushing the chamber containing the biologic sample with the wash solution. Wash solution is pumped in one fluid port and removed from the other. This process requires the presence of a "fluid injector" and a "fluid aspirator", each articulating with a fluid port. Each injector or aspirator has a piston that is capable of opening the valve positioned in the fluid port. The piston opens the valve by deflecting an elastomeric seal that occludes the orifice of the fluid port. For the purpose of washing the biologic sample, a fluid injector pushes wash solution into the chamber. The fluid aspirator captures the reagent after it has passed through the chamber. The fluid aspirator can then channel the waste wash fluid to one or more reservoirs for ultimate disposal. This washing process occurs at a "wash station" that has one fluid injector and one fluid aspirator. The injector and aspirator are mounted on to a mechanism that lowers and raises them together.

Reagent injection into the chamber occurs at a separate "reagent injection station". Two different methods for injecting reagent will be described. The first step for both methods is that a small aliquot of the desired reagent to be injected is placed in a reagent well at the fluid inlet port. In the first method, the reagent injection station includes only a fluid injector. The fluid injector is mounted on to a mechanism that lowers the injector so that the injector articulates with the fluid port on the cell. As the fluid injector is lowered, it first forms a fluid-tight seal to the fluid port. The piston on the injector then opens the valve in the fluid port. A strong momentary vacuum is then drawn through the fluid injector. The vacuum is transmitted through the fluid port into the chamber. The small amount of air in the chamber bubbles up through the reagent in the reagent well. The vacuum in the fluid injector is then released, returning the pressure above the reagent to atmospheric level. The reagent is then drawn into the chamber by the strong residual vacuum in the chamber. Bubbles do not form because there is little to no air in the chamber to form an air bubble. Alternatively, the vacuum can be drawn through a second port which is closed before the port to the aliquot is opened. In either approach, the liquid is drawn into but not through the chamber by the vacuum.

In another method of fluid injection, reagent is placed into the reagent well, as before. A fluid injector is positioned above the fluid inlet port. In addition, the fluid aspirator is positioned above the fluid outlet port. The valves of both fluid ports are opened by this process. Reagent is then pushed into the chamber by a burst of air pressure. The transient, high-pressure reagent injection avoids entrapping bubbles by forcing laminar flow of reagent through the chamber. Once the reagent completely fills the chamber, the pressure is removed and the valves are closed by disengaging the fluid injector and fluid aspirator.

Thus, in accordance with one aspect of the invention, an apparatus for adding and removing liquid reagents to and from a sample comprises a flat surface supporting the sample and a chamber forming a cavity on the flat surface, the chamber being releasably sealed to the flat surface. Fluids can be added or removed through a fluid port in the wall of the chamber. A source of negative or positive air pressure is provided in a conduit, and an actuator is able to move the fluid port and conduit relative to each other to engage the conduit and fluid ports to each other so that the two are in fluid communication.

The chamber may include a valve that is positioned at the fluid port, and the conduit may further include a piston capable of opening the valve when the conduit and port are in communication with each other. A preferred valve is a flexible element below the port which is an extension of a gasket of the chamber which seals against the flat surface.

A well capable of holding an aliquot of reagent may be provided over the fluid port. Multiple chambers may be moved relative to the actuator to position a selected chamber at the actuator.

Another aspect of the invention includes novel methods of applying reagent to a sample. In one method, a vacuum is applied to the chamber in which the sample is positioned. After application of the vacuum ceases, the reagent is allowed to be drawn into the chamber by the vacuum formed within the chamber. In a preferred approach, the vacuum is applied to the chamber through an aliquot of reagent held in a well. When application of the vacuum above the aliquot ceases, the aliquot is drawn into the chamber.

In accordance with another novel method, a sealed chamber is apposed to a flat surface supporting the sample. An aliquot of reagent is dispensed into a reagent well located above a fluid port in the chamber. A source of air pressure is applied to the fluid port to cause the reagent to be pushed through the fluid port into the chamber.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

A description of preferred embodiments of the invention follows.

Figure 1:
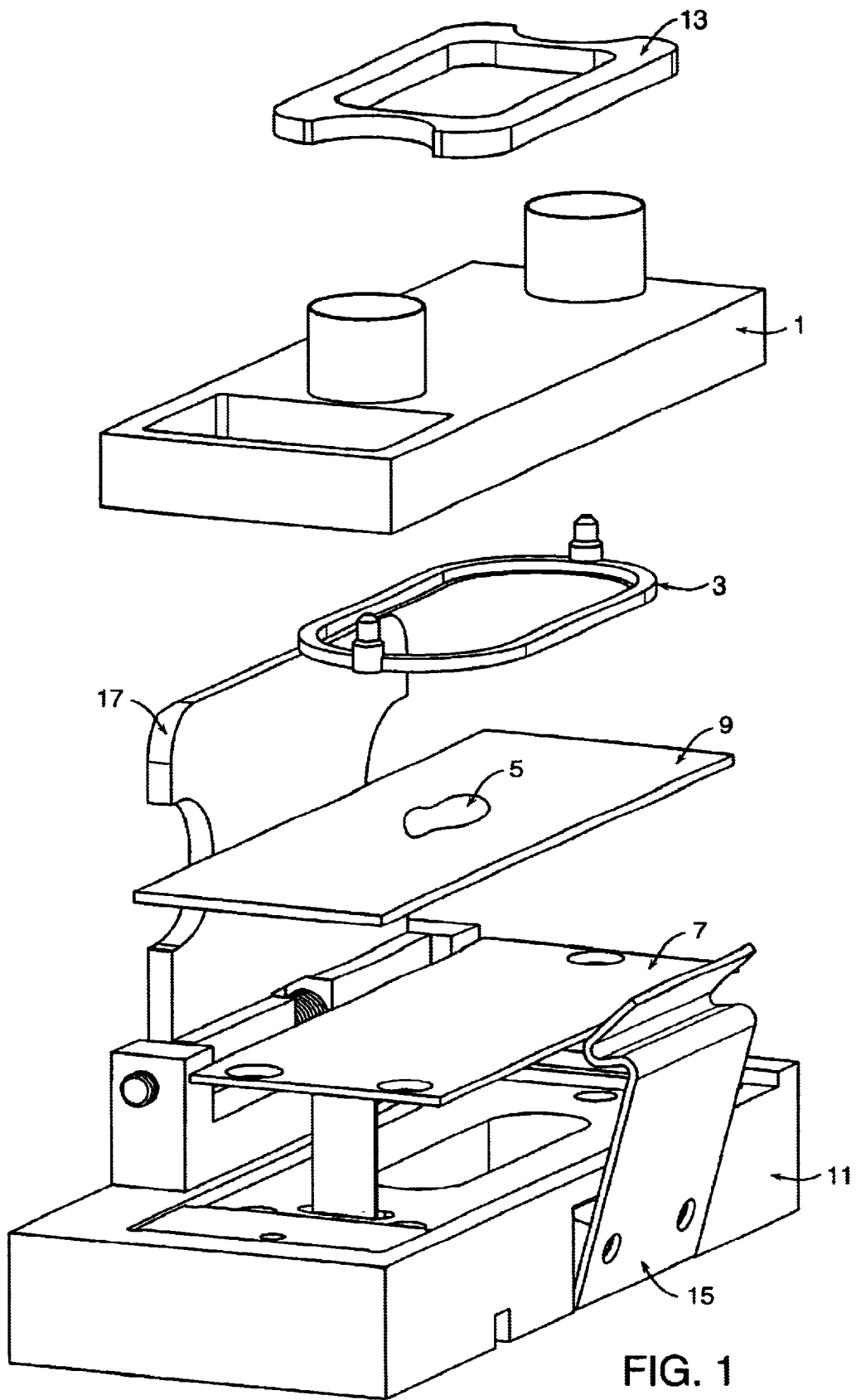
FIG. 1 is an exploded perspective drawing of the components comprising a slide nest.

FIG. 1 shows an exploded view of a complete slide nest assembly. The assembly was designed as an "ISH cell", "ISH" standing for in situ hybridization; however, it can be readily applied to other applications such as outlined in the Background. The ISH cell is comprised of a plastic cover 1 and a molded gasket 3. The gasket 3 fits into a groove (not shown) on the underside of the plastic cover 1. The ISH cell is positioned on top of a microscope slide 9 that bears a biologic sample 5 mounted on the surface of the slide. The microscope slide 9 rests on a heater plate 7. The heater plate is mounted, with screws (not shown), into a slide nest base 11. A resistive heating element (not shown) is attached to the underside of the heater plate 7. The heater plate thereby protects the electrical heater from any liquids that might spill. More importantly, the heater plate 7 diffuses the heat that emanates from the heating element to form an evenly heated surface. The thermal mass of the heater plate 7 also serves to stabilize the temperature around a desired mean temperature. Without sufficient thermal mass, actuation of the heating element can cause the temperature to overshoot the desired temperature. With some added thermal mass, as associated with the heater plate 7, the temperature rises more slowly than it would otherwise after the heating element is actuated.

Also shown in FIG. 1 is a clamping mechanism for keeping the plastic cover 1, gasket 3, and microscope slide 9 tightly apposed to each other. This clamping mechanism is important in maintaining a fluid- and air-tight seal between the plastic cover 1, gasket 3, and microscope slide 9. The clamping mechanism is formed by the hinged cover 17, foam spring 13, and latch 15. When the elements shown in FIG. 1 are fully assembled, the hinged metal clamp 17 is closed so that the end of the clamp 17 is captured by the latch 15. The clamp 17 compresses the foam spring 13 which, in turn, presses downwards on the plastic cover 1, gasket 3, and slide 9. The foam spring 13 is inserted to allow for minor variability in the dimensions of the parts shown in FIG. 1. Without the foam spring 13, too little pressure might be applied, thereby failing to form a seal. Alternatively, too much pressure might be applied, causing the microscope glass slide 9 to crack. By using the foam spring 13, the clamping mechanism is designed to slightly overcompress. The compressibility of the foam spring 13 serves to buffer that compressive force applied by the clamping mechanism, preventing the slide 9 from cracking.

Figure 2:
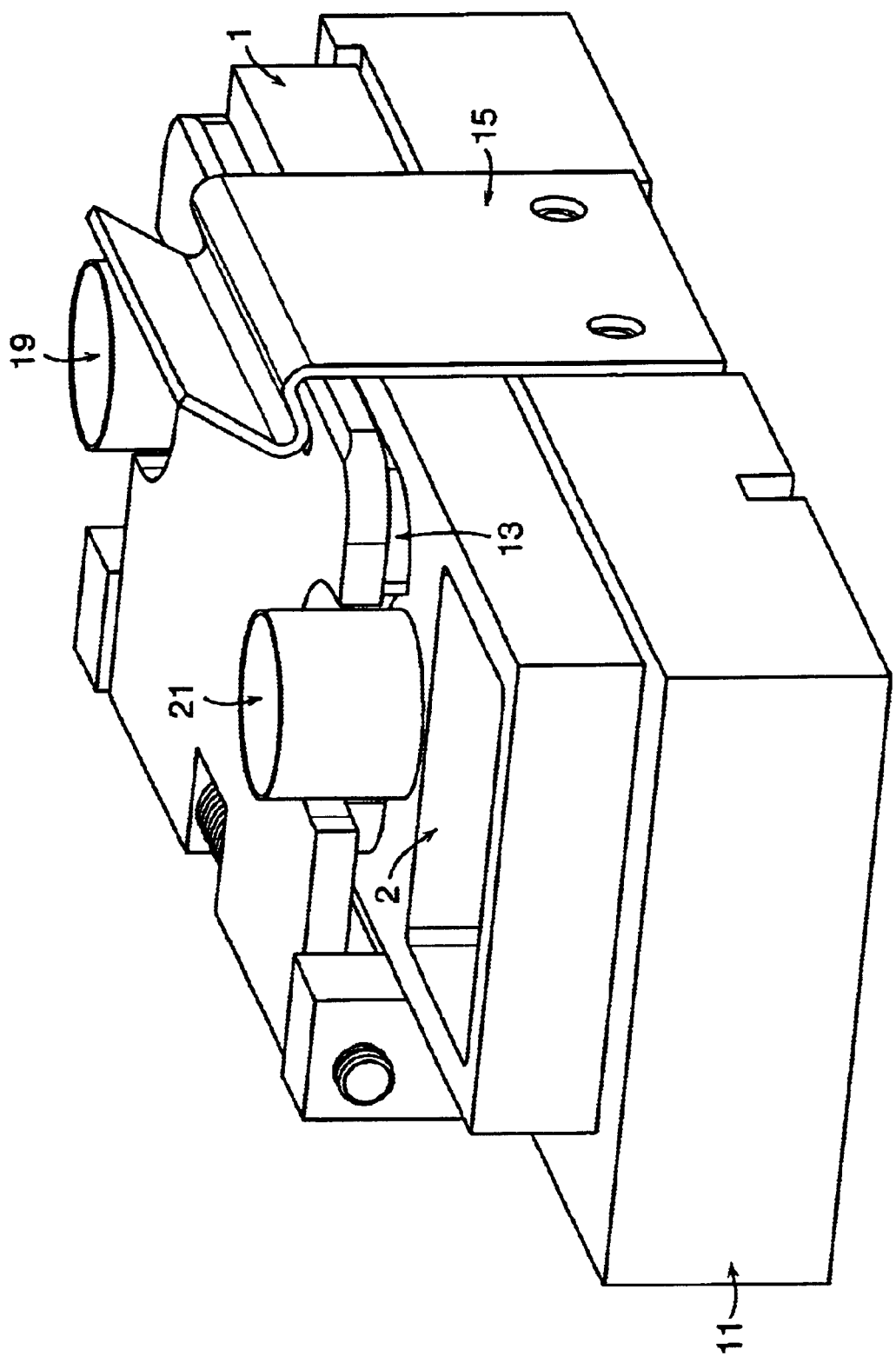
FIG. 2 is a perspective drawing of an assembled slide nest.

FIG. 2 shows the slide nest fully assembled. The clamping mechanism formed by the hinged metal clamp 17, the foam spring 13, and the latch 15 is actively maintaining the parts in fixed apposition to each other. Two fluid ports 19 and 21 protrude above the hinged metal clamp 17. An aperture 2 in the plastic cover 1 allows a direct view of a portion of the underlying microscope slide 9. The ability to view the slide 9 is for the purpose of viewing patient or sample information that might be placed on one end of the slide 9. In addition, it allows a bar code reader (not shown) to be able to view a bar code (not shown) that might be placed on one end of the glass slide 9.

Figure 4:
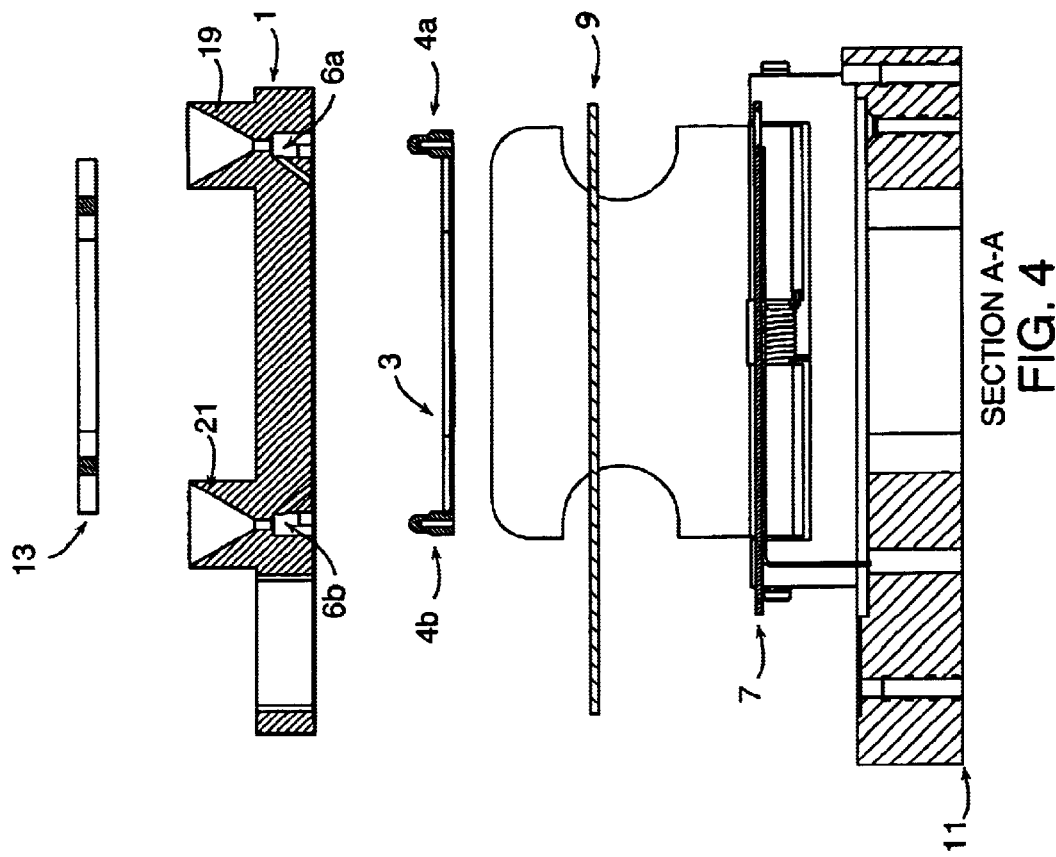
FIG. 4 is an exploded cross-sectional view of the slide nest cut through the lines A—A, as indicated in FIG. 3.
Figure 3:
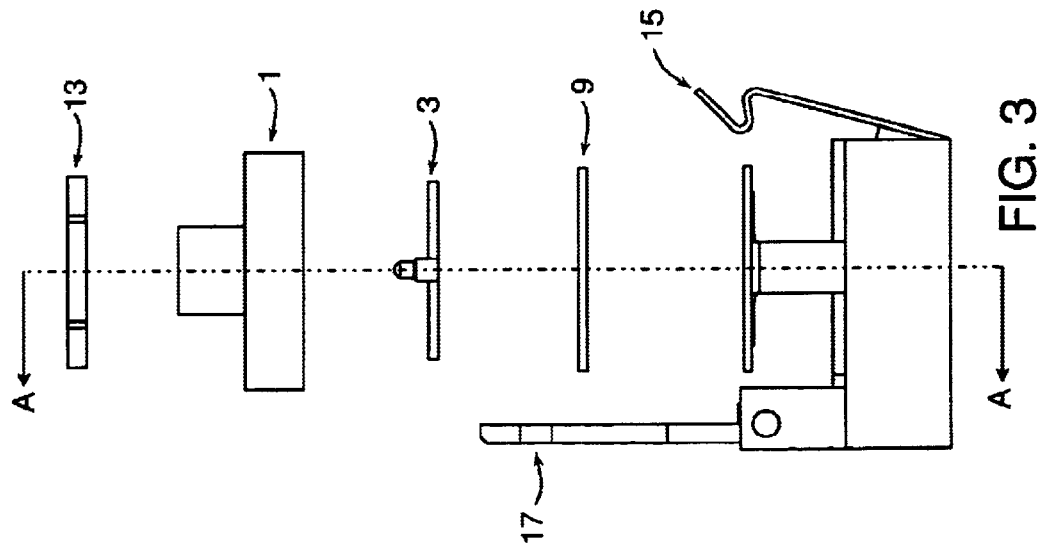
FIG. 3 is an exploded end view of the components of a slide nest.

FIGS. 3 and 4 are end and cross-sectional exploded views of the components shown in FIG. 1. These views demonstrate the presence of two elastomeric valve stems 4a and 4b that are part of the same molded gasket 3. The valve stems 4a and 4b fit into valve seats 6a and 6b, respectively. Valve seats 6a and 6b are formed as recesses in the underside of the plastic cover 1. When the valve stems 4a and 4b are inserted into valve seats 6a and 6b, the valve stems occlude fluid or air flow into or out of the fluid ports 19 and 21.

Figure 6:
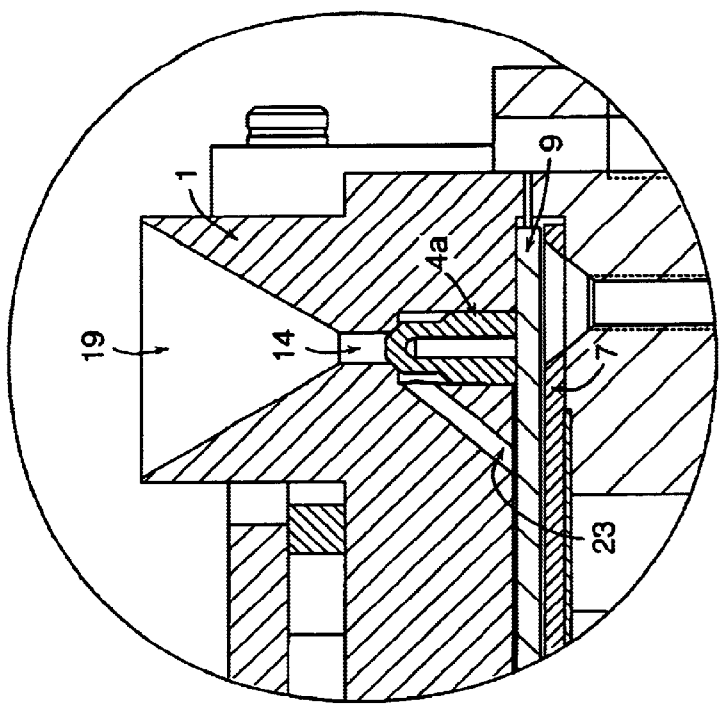
FIG. 6 is a high magnification cross-sectional view of the circled area in FIG. 5.
Figure 5:
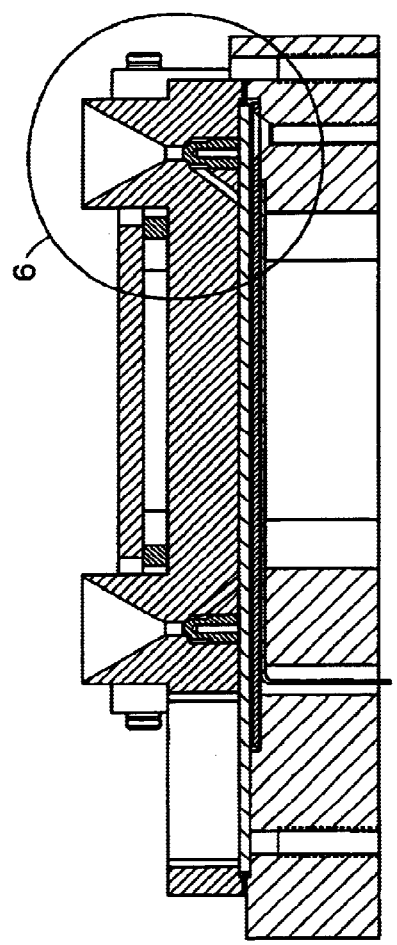
FIG. 5 is a cross-sectional view of the slide nest, fully assembled.

A better understanding of the operation of the valves associated with each of the fluid ports 19 and 21 can be obtained by reference to FIGS. 5 and 6. FIG. 5 is a cross-sectional view of the slide nest where the plane of section cuts through the valve stems 4a and 4b. A high magnification cross-section of the circled area of FIG. 5 is shown in FIG. 6. When fully assembled, the valve stem 4a fits into valve seat 6a and occludes the lowermost aspect of the neck 14 of fluid port 19. The neck 14 sits at the base of a funnel-shaped fluid port 19. When reagent is added to the fluid port 19, the funnel shape causes the reagent to collect at the bottom of the fluid port 19, towards the neck 14. Reagent can not travel past the neck 14 because the valve stem 4a blocks further flow. If the valves stem 4a were to be deflected, then reagent would be able to enter communicating passageway 23. That passageway 23 leads to the underside of the plastic cover 1 and the microscope slide 9.

Figure 7:
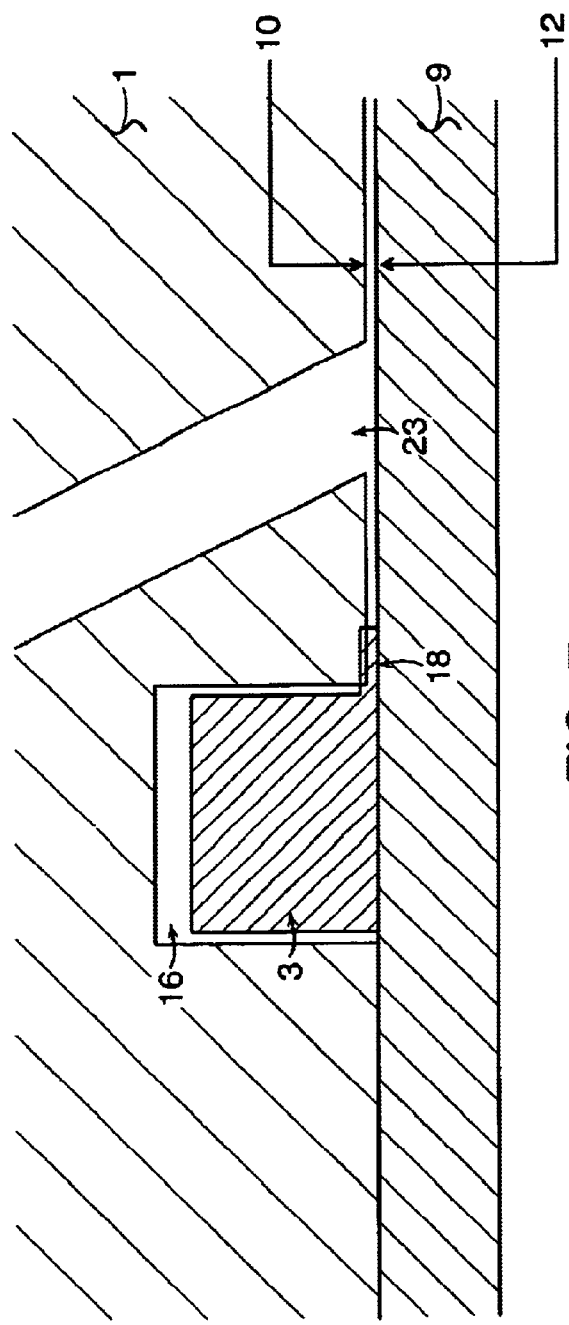
FIG. 7 is a high magnification cross-sectional view of the seal and its physical relationship to the underlying slide and overlying plastic cover.

An even higher magnification cross-sectional view of the communicating passageway 23, the gasket 3, and the chamber is shown in FIG. 7. The chamber is laterally enclosed by a perimeter formed by the gasket 3. In the illustrated embodiment, the chamber is oval-shaped. However, it can be of any convenient shape. The roof of the chamber is formed by a chamber upper surface 10 that is, in fact, the undersurface of the plastic cover 1. The chamber upper surface 10 is slightly recessed (approximately 3/1000 of an inch) relative to the undersurface of the plastic cover 1 that is not encircled by the gasket 3. The lower chamber surface 12 is, in fact, the surface of the glass slide 9. Tissue sections are typically much thinner than the height of the chamber which is preferably in the range of about 3/1000 to 6/1000 inch.

Figure 8:
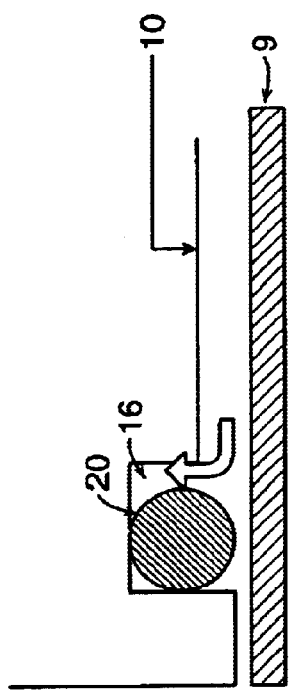
FIG. 8 is a schematic representation of an alternative, non-preferred embodiment of a seal. It is illustrated to highlight the advantages of the preferred embodiment of the seal shown in FIG. 7.

The gasket 3 fits into a gasket recess 16 that is on the underside of the plastic cover 1. The gasket 3 has a lip 18 that forms an interference fit between the upper chamber surface 10 and the lower chamber surface 12. This feature is important in limiting the volume of reagent by preventing the reagent from ever reaching the gasket recess 16 which serves to anchor the gasket 3. An acceptable, though non-preferred alternative sealing method is illustrated in FIG. 8 to illustrate the advantage of that shown in FIG. 7. If an O-ring 20 were used as a seal, then reagent would gain entry to the gasket recess 16 as illustrated by the bold arrow in FIG. 8. Some reagent would be wasted in filling the void volume of the gasket recess 16. Most of the volume of the gasket recess 16 would be occupied by the O-ring 20 itself. However, the gasket recess 16 is necessarily larger than the O-ring 20 because the O-ring 20 needs to deform as pressure is applied. Our testing disclosed that the design of FIG. 7 is superior in limiting the amount of reagent that is required to fill the chamber.

Figure 9:
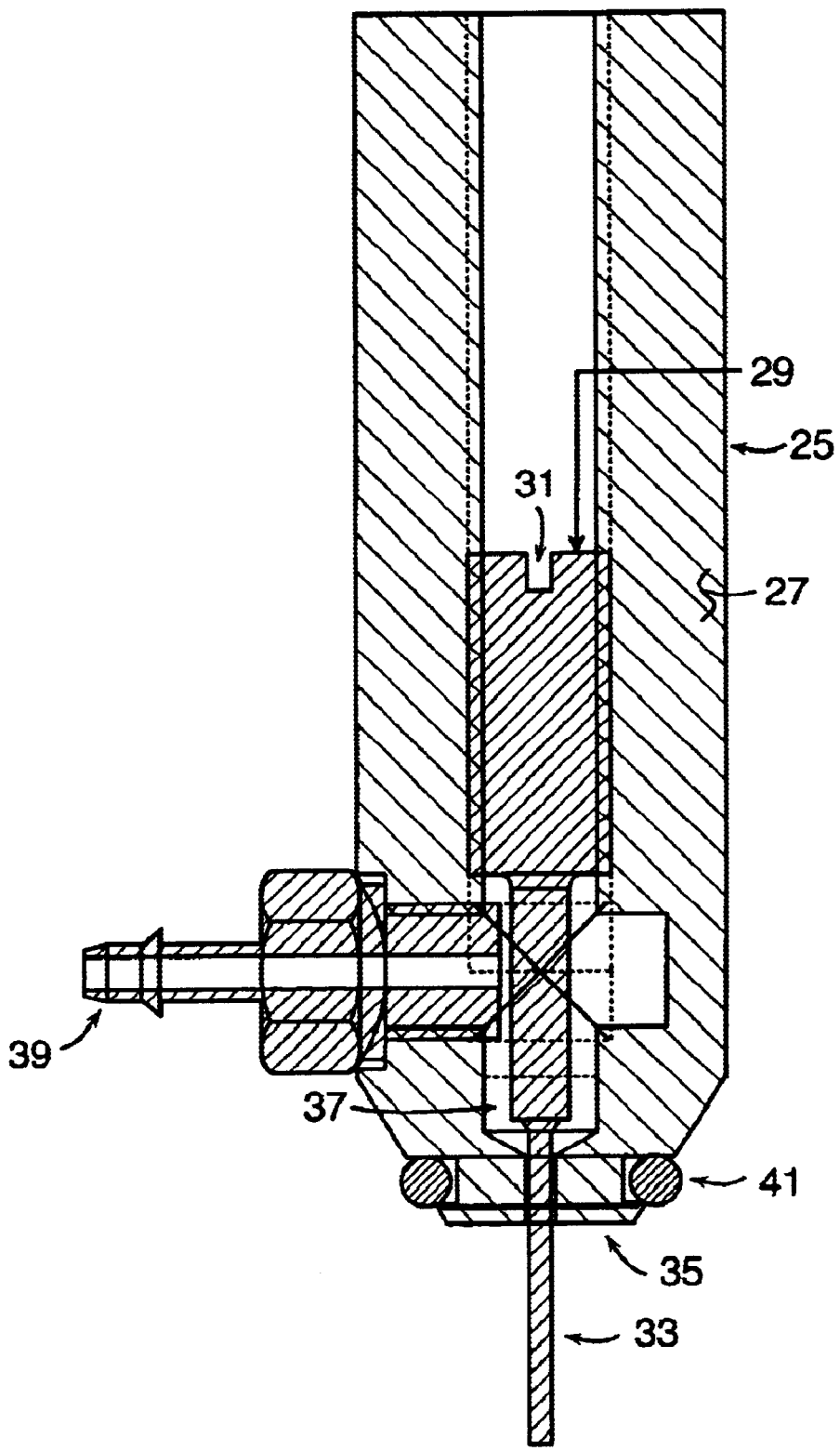
FIG. 9 is a cross-sectional representation of a fluid injector.

FIG. 9 is a cross-sectional representation of a fluid injector 25. In the illustrated and preferred embodiment, the same design is used for a fluid aspirator. The fluid injector 25 is comprised of an injector housing 27 into which a metal threaded shaft 29 is inserted. The shaft 29 fits into a hollow central core of the injector housing 27. Clockwise rotation of the shaft 29 causes the shaft 29 to move downwards, deeper into the hollow central core of the injector housing 27. Counterclockwise rotation causes the shaft 29 to move upwards. A groove 31 is provided at the top of the shaft 29 so that it can be rotated with a screwdriver. The threaded interface between the shaft 29 and the injector housing 27 is fluid- and air-tight. Consequently, air or liquid above the shaft 29 can not communicate with air or liquid around the lower portion of the shaft 29, below the threaded interface. The shaft narrows to form a piston 33 that protrudes from a lower face 35 of the injector housing 27. There is a small gap between the piston 33 and the orifice in the lower face 35 through which the piston 33 protrudes.

The fluid injector 25 also includes an air or fluid pathway, comprising a hollow side port 39 that communicates with an injector cavity 37. The cavity 37, in turn, is in communication with the orifice in the lower face 35 through which the piston 33 protrudes. The fluid injector 25 is constructed so that air or fluid pressure applied to the side port 39 will be transmitted to the orifice in the lower face 35 through which the piston 33 protrudes. Such air or fluid pressure does not travel beyond the threaded interface between the shaft 29 and the plastic body 27 because the interface is air- and fluid-tight.

Figure 10:
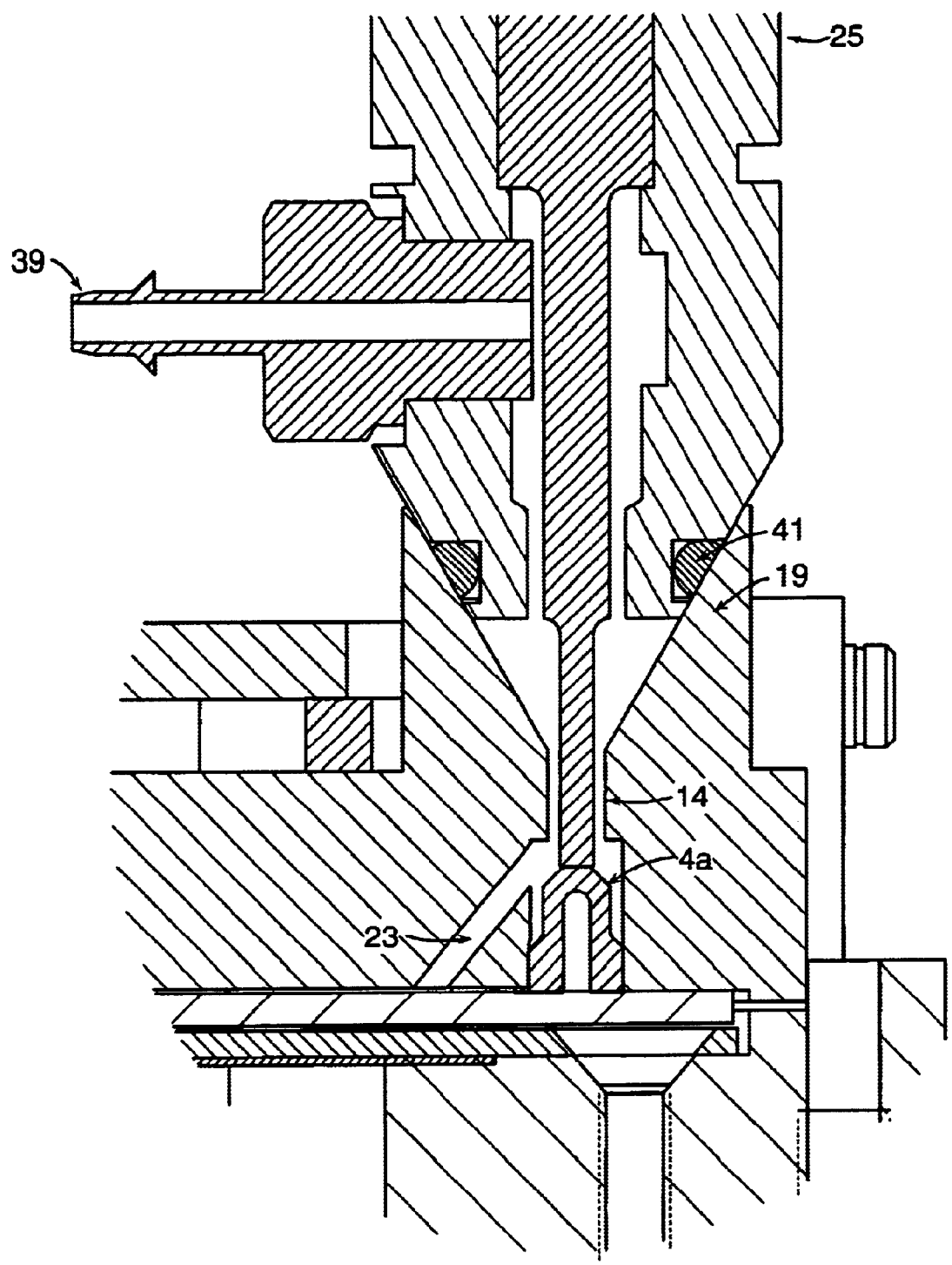
FIG. 10 is a cross-sectional representation of a fluid injector and fluid port of an ISH cell that are apposed to each other.

A elastomeric O-ring 41 is mounted towards the bottom of the fluid injector 25. This O-ring 41 is capable of forming an air- and fluid-tight seal when compressed against a conforming surface such as a fluid port 19 or 21. FIG. 10 shows the relationship of the fluid injector 25 to the fluid port 19 when the two are apposed to each other. The O-ring seal 41 compresses against the fluid port, forming an air- and fluid-tight seal. The piston 33 compresses the valve stem 4a, thereby deflecting it away from the fluid port neck 14. This opens the valve and places the hollow side port 39 in fluid and air communication with the communicating passageway 23 and the chamber.

Figure 11:
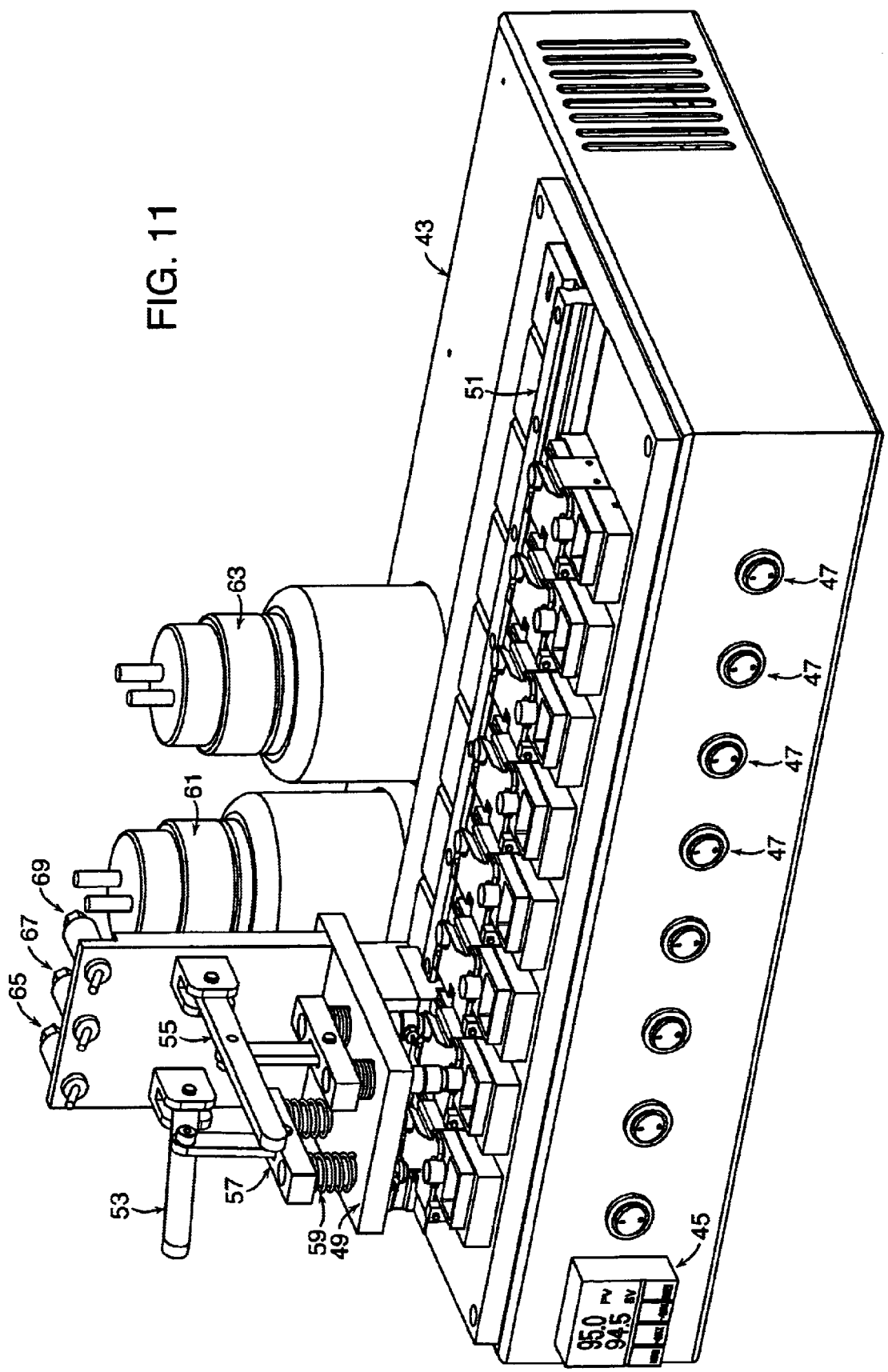
FIG. 11 is a perspective view of a slide staining instrument.

FIG. 11 is a perspective representation of an instrument 43 that incorporates positions for eight slides. The instrument 43 is shown with ISH cells in each of the eight positions. Each of the hinged covers 17 is clamped downwards underneath the latch 15. A heater controller pad 45 is located on the front panel of the instrument 43. The heater controller pad allows someone using the instrument 43 to enter a desired temperature to which the heaters will be heated. Switches 47 are also provided to turn off the heat to any slide positions that are empty. It is also envisioned that heater control circuitry can be incorporated that will allow each heater to be heated to a temperature distinct from that of other heaters. Such circuitry is described in U.S. Pat. No. 5,645,114 and U.S. patent application Ser. No. 09/032,676, filed Feb. 27, 1998, both of which are incorporated herein by reference in their entireties. The instrument 43 also comprises a moving platform 49 that slides from side to side on a track 51. The moving platform has two actuators 53 and 55. Actuator 53 is termed the "rinse actuator", and is connected to two fluid injectors by means of a mechanical linkage 57, and the linkage 57 is normally kept in an up position by two springs 59 that are mounted underneath the linkage 57.

Actuator 55 is termed the "fill" actuator and may be connected to one or two fluid injectors, depending upon the method of filling the chamber with reagent (to be described later). In each method, an aliquot of reagent is preferably placed in the well of port 19, as by an automatic pipette, before the assembly is positioned below the fill activator. If only one fluid injector is used, then a dummy injector is used in lieu of the absent fluid injector. The dummy injector is cylindrical injector housing 27, without the shaft 29 and piston 33. It is used in lieu of the fluid injector to balance the distribution of downward forces generated by the actuator 55. The actuators 53 and 55 are represented as manually-controlled handles. However, it is understood that they could also be operated by motors, under computer control. Actuator 55 is shown in the "down" position, causing a fluid injector and dummy injector to be apposed to the fluid ports 19 and 21. Thus, when the actuator 55 is in the down position, the fluid injector 25 and fluid port 19 are in the relationship as shown in FIG. 10.

Figure 12:
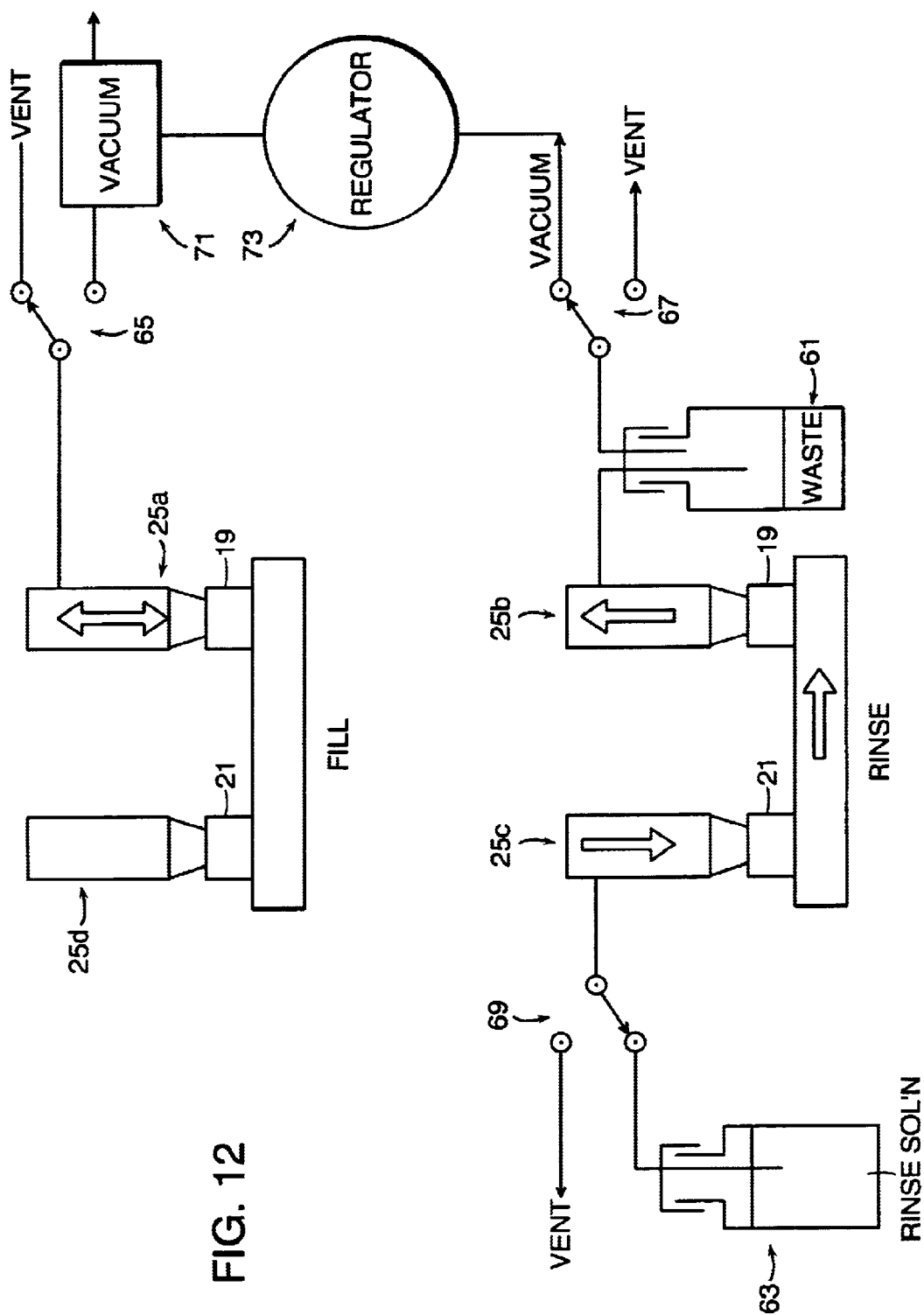
FIG. 12 is a schematic representation of the fluid pathways found in the slide staining instrument.

Also shown in FIG. 11 are two bottles 61 and 63. These bottles are connected, by flexible tubing (not shown), to the valves 65, 67, and 69 which in turn are connected to fluid injectors 25a–25c (FIG. 12) mounted on the moving platform 49. The pathways for the fluid connections are shown in FIG. 12. The upper half of FIG. 12 describes the fluid connections for the fill station. The lower half of FIG. 12 describes the fluid connections for the rinse station. Both stations require a source of vacuum pressure, not shown in the diagrams. This source is most conventionally a vacuum pump. A distribution manifold 71 for the vacuum channels the vacuum force to valve 65 and to a pressure regulator 73. Valve 65 is normally in the vent position, as shown in FIG. 12. In both the fill and rinse stations, the fluid injectors are represented in the down position, as illustrated in FIG. 10. As shown in FIG. 12, the vacuum force can be transmitted through the manifold 71 and valve 65 to the side port 39 of the fluid injector 25a in the fill station. Alternatively, the valve 65 can vent the side port 39 of the fluid injector 25a to atmosphere. The object represented as 25d can either be a "dummy" injector, as previously described, or a normally constructed injector.

Vacuum force can also be transmitted through regulator 73 to valve 67. Valve 67 provides a conduit to one side of a waste trap bottle 61. The other side of the bottle 61 is connected, via flexible tubing, to the side port of fluid injector 25b. Unless manually actuated, valve 67 connects the side port 39 of fluid injector 25b to atmosphere ("vent"). Fluid injector 25c is also part of the rinse station. Its side port 39 is connected to valve 69 via flexible tubing. The valve can either vent the line to atmosphere or connect it to bottle 63 filled with rinse solution. Unless manually actuated, valve 69 is normally connected to the bottle 63.

The method of filling and rinsing the chambers using this apparatus will now be described. This method description assumes that a slide 9 is inserted into a slide nest and clamped securely, as already described. A biologic specimen 5 or array, also as already described, is located on the surface of the slide 9. The goal is to incubate the specimen with a reagent for a defined period of time, as already described, and then remove that reagent by a rinse process. This rinse process, as already described, involves flushing the reagent away with an excess of a rinse solution. The biologic specimen 5 is contained within a sealed chamber, whose boundaries have already been described. In this section, we will describe how rinsing and reagent filling is accomplished in this context.

The explanation can best be understood with reference to FIGS. 11–12. Rinsing a specimen 5 on a slide 9 is accomplished by moving the moving platform 49 so that the rinse actuator 53 is positioned over the desired slide 9. The actuator 53 is manually depressed, causing fluid injectors 25b and 25c to be apposed to the fluid ports 19 and 21. Manually depressing the actuator thereby causes the pistons 33 of fluid injectors 25b and 25c to open the valves associated with fluid ports 19 and 21. Valve 67 is then actuated so as to connect the vacuum to the waste bottle 61. Valve 69 normally connects the rinse solution bottle 63 to the fluid injector 25c. Actuation of valve 69 is therefore not initially necessary. By pulling vacuum on fluid injector 25b, rinse solution is drawn through valve 69 and fluid injector 25c, into the chamber formed on top of the slide 9. Fluid flows in the direction of the arrow shown at the bottom half of FIG. 12. After a sufficient amount of rinse solution has passed through the chamber, valve 69 is actuated. This actuation will cause the vacuum force to pull air, rather than rinse solution, through the chamber. Thus, any rinse solution in the chamber will be aspirated, leaving an empty, air-filled, chamber. Rinse solution is collected in the waste bottle 61. The regulator 73 is important to limit the flow rate of rinse solution through the chamber. If the vacuum pressure is too high, the high flow rate of rinse solution through the chamber might potentially shear the biologic sample 5 off of the slide 9.

There are at least two methods for filling reagent into the chamber so as to incubate the biologic specimen 5 with the reagent. According to the first method, fluid injector 25d is, in fact, a "dummy" injector and does not open the valve of the underlying fluid port 21. In this first method, an aliquot of the reagent is manually dispensed into the fluid port 19. The conical shape of the fluid port serves as a reservoir to retain the reagent. Because the valve associated with the fluid port 19 is normally closed, the reagent does not initially enter into the chamber via the communicating passageway 23. The user then positions the moving platform 49 so that the actuator 55 is positioned over the fluid port 19 containing reagent. The user then depresses the actuator 55, causing fluid injector 25a, and dummy injector 25d, to mate with fluid ports 19 and 21. When the actuator 55 is depressed, fluid injector 25a has a piston 33 that opens the valve associated with the fluid port 19. At this point, the user actuates valve 65, causing a high vacuum force to be transmitted through the valve 65 and fluid injector 25a into the chamber. In order to draw a strong vacuum inside the chamber, it is important that the gasket 3 forms a good seal between the plastic cover 1 and the slide 9. Moreover, it is important that the O-ring seal 41 forms a good seal between the fluid injector 25a and the fluid port 19.

Any air inside the chamber is evacuated. The air bubbles up through the reagent filling the fluid port 19. Although a high vacuum is drawn, the air flow is negligible because the volume of the chamber is only approximately 100. To minimize the flow, the volume should preferably be less than 200 microliters. It is necessary to draw a vacuum for, at most, 1–3 seconds.

Valve 65 is then released to its normal position, venting to atmosphere. The reagent inside the fluid port 19 then experiences atmospheric pressure above it and a strong negative by vacuum force below it. This pressure differential instantaneously draws the reagent into the chamber. Since there is a near vacuum inside the chamber, no air bubbles form inside the chamber. The reagent is forced to evenly spread, filling the volume of the chamber. Because the chamber fills to eliminate the vacuum throughout the chamber, a precise aliquot of reagent need not be supplied to the well.

Figure 13:
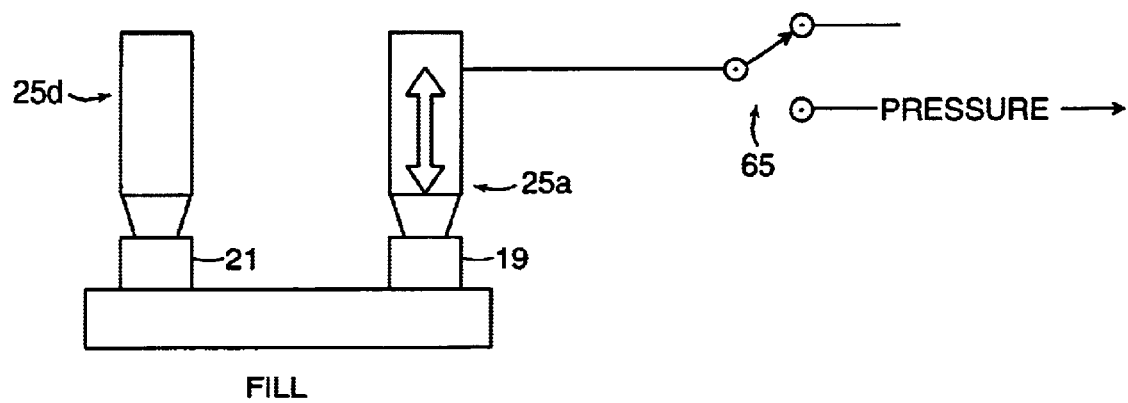
FIG. 13 is a schematic representation of the fluid pathway for reagent filling, in an alternative embodiment.

A second method for filling the chamber with reagent is characterized in FIG. 13. It requires that fluid injector 25d has a piston 33 capable of opening the valve of the underlying fluid port 21. According to this second method, reagent is manually added to fluid port 19, as before. The moving platform is also moved so that the actuator 55 is located over the fluid port 19 containing reagent. The actuator 55 is depressed, causing valves associated with both fluid ports 19 and 21 to open. In this second method, a burst of pressure drives the reagent into the chamber as port 21 is vented. Such a pressure head causes the reagent to enter the chamber in a laminar fashion. Alternatively, a short pulse of vacuum force could be applied to port 21 to pull reagent into the chamber. In either case, the pressure or vacuum should be discontinued before the reagent flows through the chamber. As yet another alternative, the vacuum could be drawn through port 21 while the valve to port 19 is held closed. Then the valve to port 21 would be closed before opening the valve to port 19 to draw reagent into the chamber.

In prior approaches, when the only pressure driving reagent into a capillary-sized chamber is the wicking action of the chamber surfaces (capillary action), then minor imperfections in the surfaces of the chamber, or the fluid drag created by the biologic specimen 5, can cause bubbles to form. The drag of the tissue sample against the weak capillary flow may be sufficient to cause the flow to pass around the sample and converge downstream of the area of fluid drag, entrapping an air bubble over the sample. If the pressure head driving the fluid flow is high relative to the fluid drag, then the fluid drag represents minor resistance as compared to the pressure head. Raising the pressure head driving reagent into the chamber thus has the result of preserving laminar flow and preventing bubbles from being entrapped.

According to this second method, valve 65 is electrically actuated so as to transiently connect to the source of pressure. The source of pressure is most conveniently a pressure pump attached to a regulator. As soon as the reagent has filled the chamber and emerged from the other fluid port 21, valve 65 is switched back. An alternative method for providing such a short, defined burst of pressure could be provided by a small syringe (not shown). The syringe plunger could be connected to an electrical actuator that rapidly drives it downwards until the plunger traverses to the bottom of the chamber. The outlet of the syringe could represent a source of a burst of pressure.

While this invention has been particularly shown and described with references to preferred embodiments thereof, it will be understood by those skilled in the art that various changes in form and details may be made therein without departing from the scope of the invention encompassed by the appended claims. For example, although valves in the assembly are particularly effective in holding the reagent in the wells, a very small hole might retain the liquid due to capillary action.

What is claimed is:

1. A method of applying reagent to a sample on a flat surface in a sealed chamber comprising:
    sealing a chamber housing to the flat surface to form a capillary sized chamber over the sample and flat surface;
    applying a vacuum to the chamber;
    ceasing to apply the vacuum while retaining the vacuum within the chamber;
    providing a supply of reagent at a port in the chamber housing; and
    after ceasing to apply the vacuum, allowing reagent to be drawn into the chamber through the port by the vacuum retained within the chamber.

2. A method as recited in claim 1 wherein the reagent is drawn from a well formed in the chamber housing.

3. A method as recited in claim 2 wherein the vacuum is applied through an aliquot held in the well.

4. A method as recited in claim 1 wherein the flat surface is a microscope slide.

5. A method as recited in claim 1 further comprising providing and retaining reagent in a well at a port into the chamber, the vacuum being drawn through the reagent in the well.

6. A method as recited in claim 1 wherein, in the step of providing the supply of reagent, an aliquot of reagent is provided in a well on the chamber wall, the well being located outside of the chamber, the port being adapted to provide fluid communication between the well and the chamber, and the chamber is subsequently moved relative to a fill station at which the step of applying the vacuum is performed.

7. A method as claimed in claim 1 wherein the height of the chamber is less than $6/1,000$ inch.

8. A method as claimed in claim 1 wherein the height of the chamber is in the range of about $3/1,000$ to $6/1,000$ inch.

9. A method of adding and removing liquid reagent to and from a sample on a flat surface, comprising:
    sealing a chamber housing to the flat surface to form a chamber over the sample and flat surface, said chamber housing having at least one fluid port, a valve in each fluid port, and a reagent well outside of the chamber in at least one of said fluid ports;
    dispensing an aliquot of reagent into said reagent well located in one of said fluid ports;
    providing a source of vacuum and a conduit that channels said source of vacuum to one of the fluid ports of the chamber housing; and
    transmitting said vacuum to the chamber housing through one of said fluid ports and the respective valve while retaining the vacuum in the chamber;
    ceasing to apply the vacuum and causing said aliquot of reagent to flow from said reagent well into said chamber by the vacuum in the chamber.

10. A method as recited in claim 9 wherein the flat surface is a microscope slide.

11. A method as claimed in claim 9 wherein, subsequent to the step of dispensing an aliquot of reagent, the chamber housing and flat surface are moved relative to a fill station at which the source of vacuum is provided and at which the step of transmitting said vacuum is performed.

12. A method as claimed in claim 9 wherein the chamber is capillary sized.

13. A method as claimed in claim 9 wherein the height of the chamber is less than $6/1,000$ inch.

14. A method as claimed in claim 9 wherein the height of the chamber is in the range of about $3/1,000$ to $6/1,000$ inch.

15. A method of processing a sample on a flat surface with a series of reagent incubations, comprising:
    sealing a chamber housing to the flat surface to form a capillary sized chamber over the sample and flat surface, said chamber housing having fluid ports at opposite ends thereof and a reagent well in at least one of the fluid ports outside of the chamber, there being a valve in each fluid port to control fluid communication to the chamber; and
    for each of the series of reagent incubations:
        dispensing an aliquot of reagent into the reagent well;
        applying a vacuum to the chamber through at least one of the fluid ports and the respective valve;
        ceasing to apply the vacuum while retaining the vacuum within the chamber and subsequently allowing reagent to be drawn from the well into the chamber through the fluid port and respective valve by the vacuum retained within the chamber;
        incubating the reagent and sample; and
        washing the sample and flat surface by forcing a wash liquid to flow through the chamber between opposite ports and respective valves.

16. A method as recited in claim 15 wherein the flat surface is a microscope slide.

17. A method as claimed in claim 15 wherein, subsequent to the step of dispensing an aliquot of reagent, the flat surface with chamber housing and a fill station, at which the step of applying the vacuum is performed, are moved relative to each other to position the flat surface with chamber housing at the fill station.

18. A method as claimed in claim 15 wherein the height of the chamber is less than 5/1,000 inch.

19. A method as claimed in claim 15 wherein the height of the chamber is in the range of about 3/1,000 to 5/1,000 inch.

20. A method as claimed in claim 15 wherein at least one of the valves is opened by a mechanical actuator.

21. A method as claimed in claim 20 wherein the mechanical actuator comprises a piston moved into the respective port.

22. A method of applying reagent to a sample in a sealed chamber comprising:

providing a well in a fluid port adapted for fluid communication with the chamber;

providing and retaining a supply of reagent in the well in the port;

applying a vacuum to the chamber through the reagent in the well and the port;

ceasing to apply the vacuum while retaining the vacuum within the chamber; and after ceasing to apply the vacuum, allowing reagent to be drawn into the chamber through the port by the vacuum retained within the chamber.

23. A method of applying reagent to a sample in a sealed chamber comprising:

providing and retaining an aliquot of reagent in a well on the chamber wall in a fluid port, the well being outside of the chamber and adapted for fluid communication with the chamber through the port;

subsequently moving the chamber and fill station relative to one another;

at the fill station, applying a vacuum to the chamber;

ceasing to apply the vacuum while retaining the vacuum within the chamber; and after ceasing to apply the vacuum, allowing reagent to be drawn from the well into the chamber through the port by the vacuum retained within the chamber.

* * * * *

UNITED STATES PATENT AND TRADEMARK OFFICE
CERTIFICATE OF CORRECTION

PATENT NO. : 6,673,620 B1 Page 1 of 1
DATED : January 6, 2004
INVENTOR(S) : Herbert H. Loeffler and Steven A. Bogen It is certified that error appears in the above-identified patent and that said Letters Patent is hereby corrected as shown below:

<u>Column 11,</u>
Line 59, after "from a well" insert -- in the port --.

Signed and Sealed this

Sixth Day of April, 2004

JON W. DUDAS
*Acting Director of the United States Patent and Trademark Office*